United States Patent
Hansen et al.

(10) Patent No.: US 9,393,096 B2
(45) Date of Patent: Jul. 19, 2016

(54) MEDICAL FILTERING DEVICES AND METHODS OF USE

(75) Inventors: Palle Hansen, Bjaeverskov (DK); Per Hendriksen, Herlufmagle (DK); Jacob Lund-Clausen, Lyngby (DK); Erik Rasmussen, Slagelse (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 94 days.

(21) Appl. No.: 14/003,075

(22) PCT Filed: Mar. 2, 2012

(86) PCT No.: PCT/US2012/027482
§ 371 (c)(1),
(2), (4) Date: Sep. 4, 2013

(87) PCT Pub. No.: WO2012/122020
PCT Pub. Date: Sep. 13, 2012

(65) Prior Publication Data
US 2013/0338703 A1    Dec. 19, 2013

(30) Foreign Application Priority Data
Mar. 4, 2011  (GB) .................................. 1103724.9

(51) Int. Cl.
*A61M 29/00* (2006.01)
*A61F 2/01* (2006.01)

(52) U.S. Cl.
CPC ........... *A61F 2/01* (2013.01); *A61F 2230/0006* (2013.01)

(58) Field of Classification Search
CPC ..................... A61F 2/01; A61F 2230/0006
USPC ................. 606/191, 194, 195, 198, 200
See application file for complete search history.

(56) References Cited

U.S. PATENT DOCUMENTS

| | | | | |
|---|---|---|---|---|
| 4,271,839 | A * | 6/1981 | Fogarty | A61M 25/0119 604/271 |
| 5,549,626 | A * | 8/1996 | Miller | A61F 2/01 606/191 |
| 6,436,118 | B1 * | 8/2002 | Kayan | A61B 17/00008 606/190 |
| 6,866,679 | B2 * | 3/2005 | Kusleika | A61F 2/95 606/108 |
| 8,066,733 | B2 * | 11/2011 | Paul | A61B 17/00008 606/192 |
| 2003/0176884 | A1 * | 9/2003 | Berrada et al. | 606/200 |
| 2007/0112374 | A1 * | 5/2007 | Paul | A61B 2/013 606/200 |
| 2007/0149996 | A1 * | 6/2007 | Coughlin | 606/200 |

(Continued)

FOREIGN PATENT DOCUMENTS

| | | |
|---|---|---|
| WO | WO 00/53120 A1 | 9/2000 |
| WO | WO 02/02162 A1 | 1/2002 |
| WO | WO 03/077799 A2 | 9/2003 |
| WO | WO 2004/110304 A2 | 12/2004 |
| WO | WO 2007/047818 A1 | 4/2007 |
| WO | WO 2008/005898 A2 | 1/2008 |

OTHER PUBLICATIONS

Extended European Search Report EP 12754387.4 (Jan. 27, 2015).

*Primary Examiner* — Katherine M Shi
*Assistant Examiner* — Mohamed Gabr
(74) *Attorney, Agent, or Firm* — Brinks Gilson & Lione

(57) ABSTRACT

A filter device for trapping embolic debris comprises a bag which is deployed by everting it from an end of a delivery catheter. After release from the catheter, with the assistance of a pusher member, the open end of the bag self-expands against the walls of a body lumen. In one method of removal after use, the device is withdrawn into catheter by pulling on a wire attached to the closed end of the bag.

15 Claims, 3 Drawing Sheets

(56) References Cited

U.S. PATENT DOCUMENTS

| | | | |
|---|---|---|---|
| 2008/0027481 A1* | 1/2008 | Gilson et al. | 606/200 |
| 2008/0065145 A1 | 3/2008 | Carpenter | |
| 2009/0306678 A1* | 12/2009 | Hardert | A61B 17/221 606/127 |
| 2010/0010534 A1 | 1/2010 | Mujkanovic | |
| 2011/0004221 A1* | 1/2011 | Euteneuer | A61B 17/0642 606/99 |
| 2013/0253573 A1* | 9/2013 | Agnew | A61F 2/01 606/200 |

* cited by examiner

MEDICAL FILTERING DEVICES AND METHODS OF USE

CROSS-REFERENCE TO RELATED APPLICATIONS

This application is a 371 national stage application of PCT Application No. PCT/US2012/027482, filed Mar. 2, 2012, which application claims the benefit of Great Britain Application Ser. No. GB 1103724.9, filed Mar. 4, 2011, entitled "MEDICAL FILTERING DEVICES AND METHODS OF USE" the entire contents of which are incorporated herein by reference.

TECHNICAL FIELD

The present invention relates to a medical device suitable for filtering materials, in particular embolic materials from the body lumens of patients.

BACKGROUND ART

When undertaking certain medical procedures, materials such as embolic debris can be inadvertently released and it is important that these do not enter and possible block blood vessels which supply the brain or other vital organs. In light of the short period of time during which brain tissue can survive without blood supply, there is significant importance to constantly providing suitable means for preventing even small embolic material from entering the carotid arteries, so as to avoid stroke and brain damage.

US 2007/0149996 discloses an example of a filtering device for collecting debris in a body lumen.

Devices in accordance with the present invention can also be used as vena cava filters, which can be retrieved via a femoral or popliteal approach.

DISCLOSURE OF THE INVENTION

Aspects of the present invention seek to provide an improved filtering device and deployment method.

According to the invention there is provided a deployment arrangement comprising a filter device and a delivery catheter therefor, the catheter having a delivery end, and the filter device having an open end and a closed end with the open end being adjacent the delivery end of the catheter, with the filter device being detached from or releasably attached to the catheter, wherein the filter device is capable of being everted upon deployment thereof from the delivery end of the catheter, and wherein the filter device is self-expanding, whereby, after eversion and deployment from the catheter, it is capable of expanding against the interior walls of a body lumen.

The filter device is preferably configured as a bag.

The material of the bag is preferably braided. This provides a structure with holes therethrough which is capable of allowing blood to continue to flow through a vessel while capturing any entrained embolic debris.

The filter device is preferably of shape memory material. This ensures that the filter device adopts its desired configuration once it is free of the catheter.

The filter device can be deployed from the delivery catheter into a body lumen by a method comprising the steps of:

inserting the filter device into the delivery catheter with an open end of the filter device being located adjacent to a delivery end of the catheter and a closed end of the filter device being located remote from the delivery end of the catheter;

everting the filter device simultaneously with deploying it from the delivery end of the catheter, and allowing the filter device to expand against the walls of the lumen.

The step of allowing the filter device to expand against the walls of the lumen may be effected gradually, so that the filter device gently unfolds along the walls of the lumen during the eversion process. Alternatively, the filter device may be fully, or substantially fully, everted before there is any substantial contact with the walls of the lumen.

The filter device can be withdrawn from a body lumen into the catheter by a method comprising the steps of:

placing the catheter inside the lumen with one end adjacent the open end of the filter device;

pulling on the closed end of the filter device from the inside thereof whereby to evert the filter device and simultaneously withdraw it into the catheter; and removing the catheter from the body lumen with the filter device inside the catheter.

The pulling step may be effected by means of a wire permanently attached to the closed end of the filter device.

Alternatively, the pulling step may be preceded by the attachment of a wire to the closed end of the filter device by suitable connection means.

In an alternative withdrawal method, the filter device is withdrawn by a pulling force on the outside of the closed end of the filter device in its deployed disposition.

BRIEF DESCRIPTION OF THE DRAWINGS

Preferred embodiments of the invention will now be described, by way of example only, with reference to the accompanying drawings, of which.

BEST MODES FOR CARRYING OUT THE INVENTION

Figure 1:
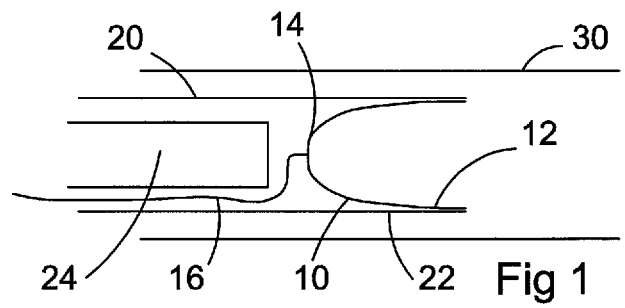
FIG. 1 shows an arrangement comprising a filter device and a catheter member in accordance with a preferred embodiment of the present invention, with the catheter member deployed in a body vessel.

Referring to the drawings, FIG. 1 shows a filter device 10 of braided shape-memory material having the general form of a tubular bag having an open end 12 and a closed end 14. The filter device is particularly suitable for use as a vena cava filter. The outside of the closed end has a wire 16 fixedly attached thereto.

The device 10 is shown inserted in a catheter member 20 which has been deployed in a body vessel or lumen 30 of a patient. The device is located adjacent to a delivery end 22 of the catheter member. Inside the catheter member, adjacent the closed end of the device 10, there is located a pusher member 24.

To deploy the filter device 10, relative movement is produced between the catheter member 20 and the pusher member 24. This can be produced by movement of the catheter member to the left in FIG. 1, or by movement of the pusher member to the right in FIG. 1, or by a combination of both movements. In the course of such movements, the material of the filter device is everted so that the outside of the bag in FIG. 1 becomes the inside of the bag in FIG. 2.

Figure 3:
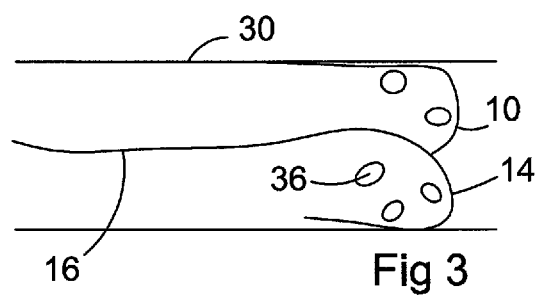
FIG. 3 shows the filter device of FIGS. 1 and 2 in use.

Once the bag has left the catheter member 20, the shape memory effect of the bag material comes into action and the filter device expands and becomes tightly braced against the interior wall of vessel 30, see FIG. 3. The filter device 10 is thus deployed in its position of use where it collects embolic debris 36.

The size of the filter device 10 depends upon the size of the body lumen 30 to be filtered. For cranial applications, the expanded diameter of the device 10, i.e. from the top of the bottom in FIG. 3, lies within the range 5 to 15 mm. For use in pulmonary vessels, the expanded diameter of the device 10 lies within the range 15 mm to 30 mm.

Catheter member 20 and its associated pusher member 24 can conveniently be completely removed from the patient.

Figure 4:
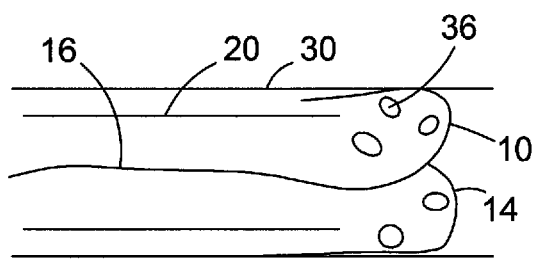
FIG. 4 shows an initial stage in the removal process of the filter device.

To remove the filter, catheter member 20 is moved back into position, FIG. 4. By exerting a pulling force on wire 16 to the left in FIG. 4 (which will generally be the femoral direction) one first reaches the disposition shown in FIG. 5 and then the disposition shown in FIG. 6. Instead of an abrupt separation of the material of filter bag 10 from the interior body vessel walls, only a relatively gentle peeling force is applied at locations 38 at the circumference of the bag as it is withdrawn, see FIG. 5. In FIG. 6, the filter bag 10 has been everted back to its original state, with its closed end 14 at the left of the FIGS., and is withdrawn into the end 22 of the catheter member. The entire assembly is then withdrawn.

Some of the embolic material 36 will attach itself to the inside of the filter bag in use in its FIG. 3 disposition. Moreover, as the filter bag moves between its FIG. 4 and FIG. 5 dispositions, some loose embolic material will be entrained therewith into the catheter member 20. However, to avoid any danger of unwanted release of embolic material into the body vessel, the embolic material is preferably flushed away while the filter bag is still in its FIG. 3 disposition. This can be effected by dissolving away the embolic debris.

Figure 2:
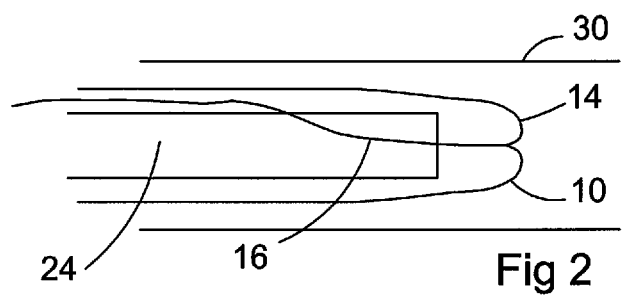
FIG. 2 shows the arrangement of FIG. 1 after deployment of the filter device from the catheter member.

An advantage of the above described arrangement is that the catheter member 20, and the other parts of the introducer arrangement including pusher member 24, can be completely removed between the deployment, FIG. 2, and removal (FIG. 4) phases of the filter device 10. This leaves the vasculature free for other medical interventions.

Figure 5:
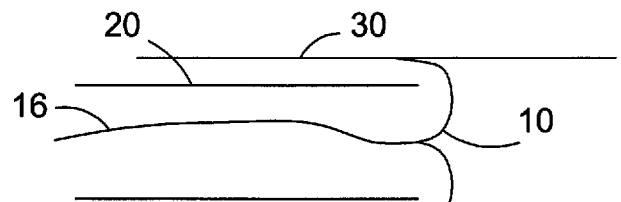
FIGS. 5 and 6 show stages subsequent to FIG. 4 in the removal process of the filter device.
Figure 6:
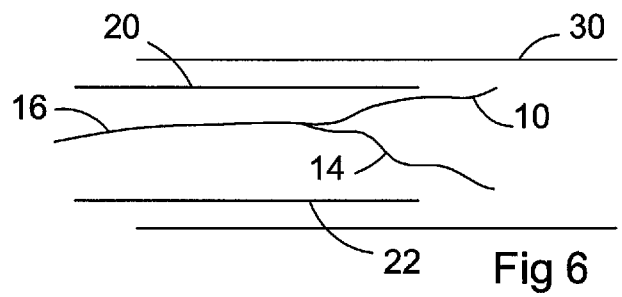

Another advantage of the arrangement is the gentle removal procedure described in correction with FIGS. 5 and 6. Because filter device 10 comprises braided material, some growth of the body wall around the device may have occurred between deployment and removal. Because the removal of the material of the device consists of gently peeling it from the walls of the body vessel 30, minimal damage is caused to the vessel wall.

The deployment and withdrawal procedures of the filter device are relatively simple. Once the introducer arrangement comprising the catheter member 20 has been deployed, FIG. 1, a single relative movement of the components effects complete deployment of the filter bag 10, FIG. 2.

The change between the configurations of the filter device 10 in FIGS. 2 and 3 may be a relatively sudden one. However, in one preferred arrangement, the walls of the filter device gradually engage the walls of the body lumen as the device is everted, and unfold relatively slowly theralong. This is substantially the opposite of the previously described withdrawal process and has the advantage of reducing trauma for the patient.

Figure 7:
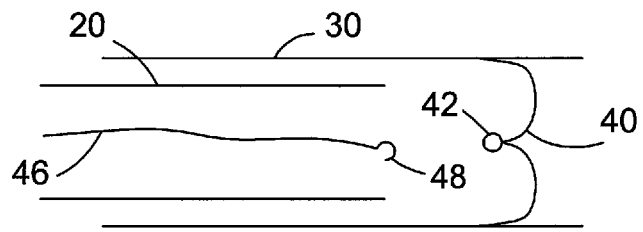
FIGS. 7 and 8 show alternative removal processes to that of FIGS. 4 to 6.

In a modified arrangement, a filter device 40, FIG. 7, is installed without a wire 16. The device has a loop 42 at its closed end. When it is desired to remove the device 40, a wire 46 with a hook 48 at its end is advanced through catheter 20 and into the device 40. The loop 42 is snared by the hook 48, and the filter device is then withdrawn as shown in FIG. 6. An advantage of this modification is that, between the deployment and withdrawal procedures, it is not necessary to leave a wire 16 in the patient's vasculature. The positions of the hook and loop may be interchanged, and any other suitable connection arrangement can be employed.

Figure 8:
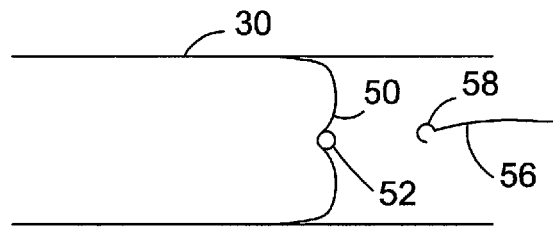

In an alternative modification, a filter device 50, FIG. 8, has a loop 52 on the other side of the closed end. When it is desired to remove the device 50, a wire 56 with a hook 58 at its end is advanced thorough the patient's vasculature, typically from the jugular direction. The loop 52 is snared by the hook 58 and the filter device is withdrawn to the right in FIG. 8. It will be noted that the filter device is not everted during this withdrawal procedure. The same modifications can be made as described in connection with FIG. 7.

Alternatively, if desired, the filter device may be left permanently in the patient's body lumen 30, and may be provided with barbs to ensure long-term retention.

Figure 9:
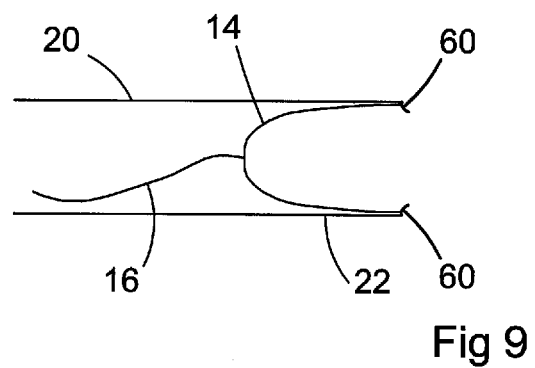
FIG. 9 shows a modified arrangement of a filter device and associated catheter member.

In other modified arrangements, the mouth of filter bag 10 is releasably attached to the delivery end 22 of catheter 20 by means of one or more circumferential hook members 60, FIG. 9. The hook members 60 are configured to maintain open the mouth of the bag 10 as it is moved between its dispositions shown in FIGS. 1 and 2. When the bag 10 reaches its FIG. 2 disposition, the shape and orientation of the hook members 60 are such that they are automatically released from the bag.

The filter device 10 is preferably made of a shape memory material such as Nitinol. Alternatively it can be made of a resilient material such as stainless steel or cobalt-chronium etc. This also has advantages of ensuring a good seal between the filter device and the body lumen walls.

The filter device does not need to be braided. It can have a mesh or any other suitable perforated structure.

The filter device can be coated and/or impregnated with a substance which resists restenosis or minimises ingrowth.

The disclosures in United Kingdom patent application no. 1103724.9, from which this application claims priority, and in the abstract accompanying this application are incorporated herein by reference.

The invention claimed is:

1. A deployment arrangement comprising a perforated filter device and a delivery catheter therefor, the catheter having a delivery end, and the filter device having an open end and a closed end, the deployment arrangement having a delivery configuration with the open end of the filter device having a shorter distance from the delivery end of the catheter than a distance of the closed end from the delivery end of the catheter, the closed end disposed within the catheter, with the filter device being detached from or releasably attached to the catheter, wherein the deployment arrangement has a deployed configuration, wherein the filter device is everted upon deployment from the delivery end of the catheter such that the open end of the filter is closer to the delivery end of the catheter relative to the closed end and the closed end is disposed outside of the catheter, and wherein the filter device is self-expanding, whereby, after eversion and deployment from the catheter, the open end is detached from the catheter and the filter device including the open end self-expands against the interior walls of a body lumen.

2. An arrangement according to claim 1, wherein the filter device is configured as a bag.

3. An arrangement according to claim 2, wherein the material of the bag is braided.

4. An arrangement according to claim 1, wherein the filter device is of shape memory material.

5. An arrangement according to claim 1, wherein the filter device is of resilient material.

6. An arrangement according to claim 1, wherein the open end of the filter device and the delivery end of the catheter are attached by one or more releasable attachment members.

7. An arrangement according to claim 1, further including a pusher member arranged within the catheter so as to be axially displaceable relative thereto to engage the filter device.

8. A method of deploying a filter device from a delivery catheter into a body lumen, with the filter device being detached from or releasably attached to the catheter, the catheter having a delivery end, and the filter device having an open end and a closed end, comprising the steps of:
 inserting the filter device into the delivery catheter with the open end of the filter device being located at a shorter distance from the delivery end of the catheter than a distance of the closed end of the filter device from the delivery end of the catheter;
 everting the filter device simultaneously with deploying it from the delivery end of the catheter, and
 allowing the filter device, including the open end of the filter device, to expand against the walls of the lumen.

9. A method according to claim 8, wherein a pusher member is used to evert the filter device.

10. A method according to claim 8, wherein the step of allowing the filter device to expand against the walls of the lumen is effected gradually during the eversion process.

11. A method according to claim 8 wherein the filter device is substantially fully everted before there is any substantial contact with the walls of the lumen.

12. A method of withdrawing a deployed filter device from a body lumen into a catheter the filter device having an open end and a closed end, comprising the steps of:
 moving the catheter inside the lumen toward the filter device from a side of the open end of the filter device with one end of the catheter closer to the open end of the filter device than to the closed end of the filter device;
 pulling on the closed end of the filter device from an inside of the filter device, everting the filter device and simultaneously withdrawing the filter device into the catheter; and
 removing the catheter from the body lumen with the filter device inside the catheter.

13. A method according to claim 12, wherein the pulling step is effected by means of a wire permanently attached to the closed end of the filter device.

14. A method according to claim 12, wherein the pulling step is preceded by the attachment of a wire to the inside of the closed end of the filter device by a connection means, the wire being subsequently used in the pulling step.

15. A method according to claim 12, wherein the pulling step is preceded by the attachment of a wire to the outside of the closed end of the filter device by a connection means, the wire being subsequently used in the pulling step.

* * * * *